United States Patent [19]

Wright et al.

[11] Patent Number: 4,524,620
[45] Date of Patent: Jun. 25, 1985

[54] IN-FLIGHT MONITORING OF COMPOSITE STRUCTURAL COMPONENTS SUCH AS HELICOPTER ROTOR BLADES

[75] Inventors: Dale M. Wright, Folsom, Calif.; Robert L. Kiraly, Mesa, Ariz.

[73] Assignee: Hughes Helicopters, Inc., Culver City, Calif.

[21] Appl. No.: 464,343

[22] Filed: Feb. 7, 1983

[51] Int. Cl.³ .................... G01N 29/04; G01M 5/00
[52] U.S. Cl. ........................... 73/587; 73/583; 416/61
[58] Field of Search ............... 73/583, 587, 801, 802; 416/61; 340/679, 683; 364/508

[56] References Cited

U.S. PATENT DOCUMENTS

| | | | |
|---|---|---|---|
| 3,713,127 | 1/1973 | Keledy et al. | 73/587 |
| 3,744,300 | 7/1973 | Fleury | 73/583 |
| 4,106,332 | 8/1978 | McKeown | 416/61 |
| 4,297,885 | 11/1981 | Hein et al. | 73/587 |
| 4,336,595 | 6/1982 | Adams et al. | 73/802 |

OTHER PUBLICATIONS

Burkhardt et al., "Acoustic Methods for Obtaining Barkhausen Noise Stress Measurements", *Materials Evaluation*, 40, May 1982, pp. 669–675.

*Primary Examiner*—Jerry W. Myracle
*Assistant Examiner*—John E. Chapman, Jr.
*Attorney, Agent, or Firm*—Beehler, Pavitt, Siegemund, Jagger & Martella

[57] ABSTRACT

The apparatus comprises one or more acoustical transducers associated with a particular interchangeable rotor blade for monitoring acoustic emissions emitted by the rotor blade under operating stress. The output of the transducers is connected to a computer associated with the particular aircraft. The transducer output signals are processed by the computer and filtered to allow real time stress return level readings so as to accumulate a count of critical acoustic emissions which are indicative of progressive irreversible structural fatigue or damage to the interchangeable rotor blade.

4 Claims, 3 Drawing Figures

IN-FLIGHT MONITORING OF COMPOSITE STRUCTURAL COMPONENTS SUCH AS HELICOPTER ROTOR BLADES

BACKGROUND OF THE INVENTION

1. Field of the Invention

The present invention concerns method and apparatus for in-flight acoustical monitoring of structural components in aircraft and more particularly is directed to a method and apparatus for measuring the actual remaining useful life of interchangable dynamic structural aircraft components, particularly helicopter rotor blades.

2. State of the Prior Art

It is known in the art to monitor acoustic emissions emitted by structures subject to loads in order to detect cracking or other failure in the structure. Typical instrumentation for carrying out such acoustic emission monitoring is disclosed by the following patents, which are primarily concerned with the transducer elements necessary to convert mechanical vibration to an electrical output for processing by suitable electronic circuits:

| U.S. Pat. No. | Patentee | Issued Date |
| --- | --- | --- |
| 3,774,443 | Green et al | November 27, 1973 |
| 3,855,847 | Leschek | December 24, 1974 |
| 3,779,071 | Thomas Jr. et al | December 18, 1973 |
| 3,529,465 | Kleesattel et al | September 22, 1970 |
| 4,088,907 | Jones et al | May 9, 1978 |

A typical electronic circuit for processing acoustic emission signals is disclosed in U.S. Pat. No. 3,924,456 issued to Vahaviolos Dec. 9, 1975.

The need to monitor aircraft structures in order to detect or anticipate structural damage or failure before the aircraft ceases to be flightworthy has long been recognized as exemplified by U.S. Pat. No. 3,387,120 to Funk et al issued June 4, 1968 and U.S. Pat. No. 3,596,269 to Laska issued July 27, 1971. Both these patents disclose electronic or electro mechanical monitoring systems. Laska uses resistive components which are applied to critical surfaces such that the resistive components break upon failure of the structural member of interest. The resulting change in resistance is detected by appropriate circuitry and an indication of such failure is made to the aircraft crew. Funk et al discloses a system which measures acceleration loads imposed on the air frame and alerts the crew to excessive stresses. A circuit similar in principle to that of Laska is also disclosed in U.S. Pat. No. 4,106,332 issued to McKeown on Aug. 15, 1978.

The use of acoustic monitoring for testing of aircraft structures is disclosed as early as May 19, 1936 in U.S. Pat. No. 2,040,874 issued to Pack. The system disclosed therein, however, is not suited for continuous in-flight monitoring of the structure and is further limited to measuring resonant frequencies of structural members in response to an artificial mechanical stimulus which excites the member into a vibration mode.

The need to monitor the structural integrity and fatigue damage in helicopter rotor blades has been also recognized and solutions proposed in U.S. Pat. No. 3,744,300 issued to Fleury on July 10, 1973 and also in U.S. Pat. No. 3,985,318 issued to Dominey et al on Oct. 12, 1976. Fleury uses a resistive sensor for measuring progressive fatigue damage experienced by the rotor blade while Dominey et al uses a pressure differential sensing approach for use with hollow rotor blades the interior of which is at a pressure other than atmospheric such that cracks may be detected by the fact that the interior of the blade will be at atmospheric pressure. These two approaches suffer from obvious deficiencies in that Fleury is limited to sensing damage in the immediate area to which the resistive sensor is applied and would ignore changes in the structure occurring in areas removed from the sensor. Dominey et al is limited to blades in which a pressure differential can be maintained and is further deficient in that only an actual crack through the skin of the rotor blades sufficient to cause pressure equalization is capable of being detected. Progressive damage short of such a crack is not susceptible to detection by this system. The Fleury system is based on a determination of the number of force cycles to which the blade is subjected and on the amplitude of the force experienced in each cycle. This type of approach cannot detect progressive failure of a structural member occurring, for example, as a result of moisture infiltrating the interior of the structural member and causing degradation of adhesive bonds or corrosion of metallic structures. This kind of weakening is not a result of forces to which the blade is subjected and, therefore, would escape detection with this type of system.

A continuing need, therefore, exists for an in-flight monitoring system capable of monitoring progressive fatigue damage and deterioration of dynamic aircraft components and predicting actual failure of the structure prior to the occurrence of gross faults such as cracks required to trigger the Dominey et al system.

The need for reliable in-flight monitoring systems has become particularly acute in recent times with increasing use of composite materials in aircraft structures which are assembled through methods not yet fully tested, as opposed to welding, riveting and time proven assembly methods. Typically, composite materials are assembled by high temperature curing of epoxies which involve processes relatively novel to the aircraft industry and thus requiring the highest possible level of care to avoid accidents caused by unpredictable failure of structures for which no reliable life expectancy base lines have been established.

SUMMARY OF THE INVENTION

The present invention overcomes the deficiencies of the prior art by providing a method and apparatus for determining the actual remaining useful life of interchangeable helicopter rotor blades. The present invention further overcomes the problem of providing real time warning to the aircraft crew of impending rotor blade failure based on an acoustic emission history of the particular blade. This problem is not addressed in the known prior art and is of importance where prediction of failure is based on the history of the particular blade because such rotor blades are often removed from a particular helicopter for minor repair and maintenance, such as replacement of the leading edge erosion strip of the rotor blade and are then mounted on different helicopters.

The apparatus of the invention, therefore, comprises one or more acoustical transducers means associated with a particular interchangable rotor blade for monitoring acoustic emissions emitted by the rotor blade under operating stress. The output of the transducers is connected to a computer associated with the particular aircraft. The transducer output signals are processed by the computer and filtered to allow real time stress return level readings in a manner known to the art so as to accumulate a count of critical acoustic emissions which are indicative of progressive irreversible structural fatigue or damage to the interchangable rotor blade.

Indicator devices are provided for displaying the accumlated count to the crew of the aircraft, preferably as a percentage of a predetermined maximum count which has been reliably established as a safe level of accumulated structural aging, but beyond which the likelihood of catastrophic structural failure of the rotor blade increases substantially. In this manner the particular rotor blade may be used through substantially all of their useful life as determined by actual aging of the rotor blade. The aging process may proceed at greatly different rates for blades used under different operating conditions. For example, rotor blades used in combat maneuvers are subject to operating stresses vastly greater than rotor blades which are used in routine transport missions in a nonhostile environment.

At the present time, helicopter rotor blades are routinely replaced after a certain arbitrary number of flight hours irrespective of the flight conditions underwhich the blades were used. It is believed that through actual monitoring of the individual rotor blades in the manner disclosed in the present specification an extension of two to five times may be achieved in the number of flight hours obtained from the average rotor blade. Similarly, some rotor blades may have manufacturing defects or structural flaws which may call for early replacement of the particular blade to thus prevent accidents. At the present time, rotor blades are flown typically for approximately 4,500 hours per rotor blade.

Main rotor blades are costly items in that they are complex structures made of composite materials such as Kevlar ® (a registered mark of the DuPont Chemical Co.). Typically, a single main rotor blade for the new U.S. Army Advanced Attacked Helicopter AH-64A costs approximately $30,000 with four main rotor blades being required for each helicopter. It will be readily appreciated that a doubling in the useful life of a set of rotor blades can result in substantial savings.

A life expectancy fixed in terms of a fixed number of flight hours per rotor blade fails to recognize that different pilots, missions, and weather conditions affect rotor blades differently. For example, evasive action maneuvers greatly accelerate structural deterioration of rotor blades as compared with point to point routine flight.

The United States Army has presently contracted for 515 of the advanced attack helicopter ships. With each set of main rotor blades costing $120,000 the initial expenditure on rotor blades for this program is expected to be of the order of $61,800,000 (not including spares). It is estimated that each set of blades will be replaced approximately four times for each helicopter, based on past experience. Blade replacement is the most expensive component of helicopter maintenance, in terms of the cost of replacement blades and time and labor required to make the replacement. Clearly very substantial savings can be realized by extending the useful life of rotor blades.

Presently all fatigue testing of rotor blades is conducted on the ground and acoustic emission tests have been successful in predicting failure of rotor blade structures as well as in localizing such failure. Acoustic monitoring is often capable of detecting defects not observable by X-ray examination, or other inspection techniques.

Preferably the computer further comprises data storage means for storing the accumulative count of acoustic emissions such that the count of critical acoustic emissions over many flights of the particular helicopter is retained in the computer and displayed as a steadily increasing percentage of a maximum acceptable total accumulated stress.

The computer may further include appropriate data input means for entering a base count into the data storage means so as to make it feasible to enter the prior stress history of a previously used rotor blade newly mounted to the particular helicopter. Helicopter blades are frequently interchanged between different helicopters over the lifetime of the rotor blade. Particular rotor blades are removed from helicopter for repairs such as repainting or replacement of the erosion strip. This procedure becomes necessary particularly when the helicopter is flown in rain or in a dusty environment including desert areas where the sand rapidly erodes the leading edge of the rotor blades. This leading erosion strip is a sacrificial portion of the rotor blade structure and requires periodic replacement. After repair the rotor blades may be installed on a different helicopter, so that the accumulated count representative of the stress history of the rotor blade must be entered into the data storage of the new helicopter.

The method of the present invention by which the safe use of interchangable helicopter rotor blades is extended, comprises the steps of installing a particular rotor blade on a first helicopter; detecting acoustic emissions emitted by the rotor blade under operating stress, and selecting those acoustic emissions indicative of progressive fatigue or aging of the rotor blade. The acoustic emissions selected are counted and the acumulated count is stored in a data storage device associated with the first helicopter. The acoustic emission count is displayed for viewing by crew members of the helicopter so as to forewarn the same in the event that the count approaches a maximum safe number.

The method further comprises removing the particular rotor blade from the first helicopter for maintenance or other purposes and installing the rotor blade on a second helicopter. It is understood that this second helicopter may actually be the same aircraft as the first helicopter, but in which the previously stored accumulated count was erased during interim use of a different set of rotor blades.

The accumulated count initially stored in the data storage associated with the first helicopter is then entered into a data storage associated with the second helicopter. The newly installed rotor blades are again monitored for further acoustic emissions emitted under operating stress and indicative of continued progressive structural damage to the rotor blade. The acoustic emissions detected are added to the previously entered count and the count so updated is made available to the crew of the second helicopter.

BRIEF DESCRIPTION OF THE DRAWINGS

FIG. 3 is a cross sectional view taken along line 3—3 in FIG. 2.

DETAILED DESCRIPTION OF THE INVENTION

Figure 1:
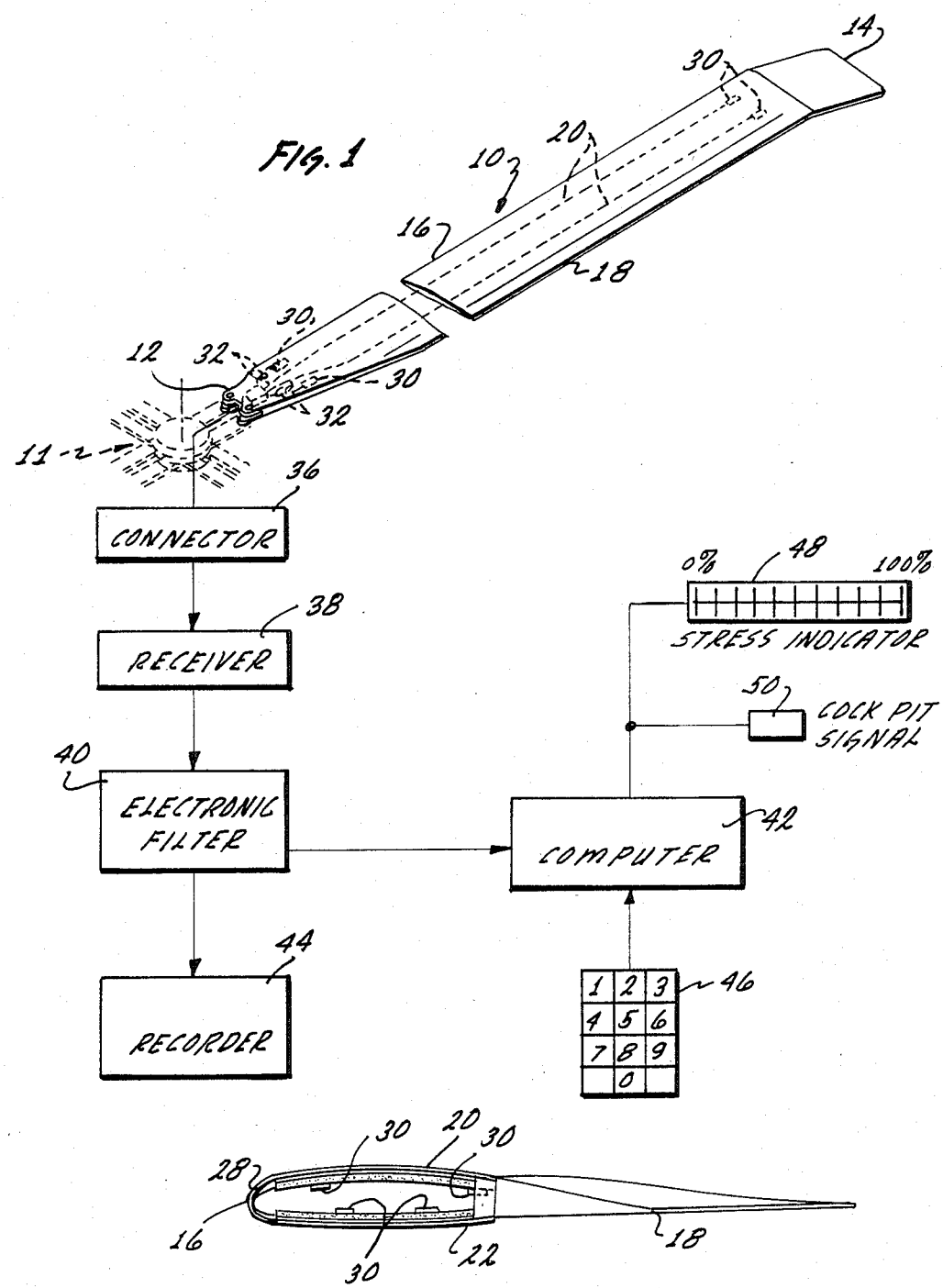
FIG. 1 illustrates a typical helicopter main rotor blade mounted to a rotor hub and provided with a set of transducers installed for monitoring acoustic emissions, and a block diagram of an electronic circuit system for processing and displaying an accumulated count of such acoustic emissions.
Figure 2:
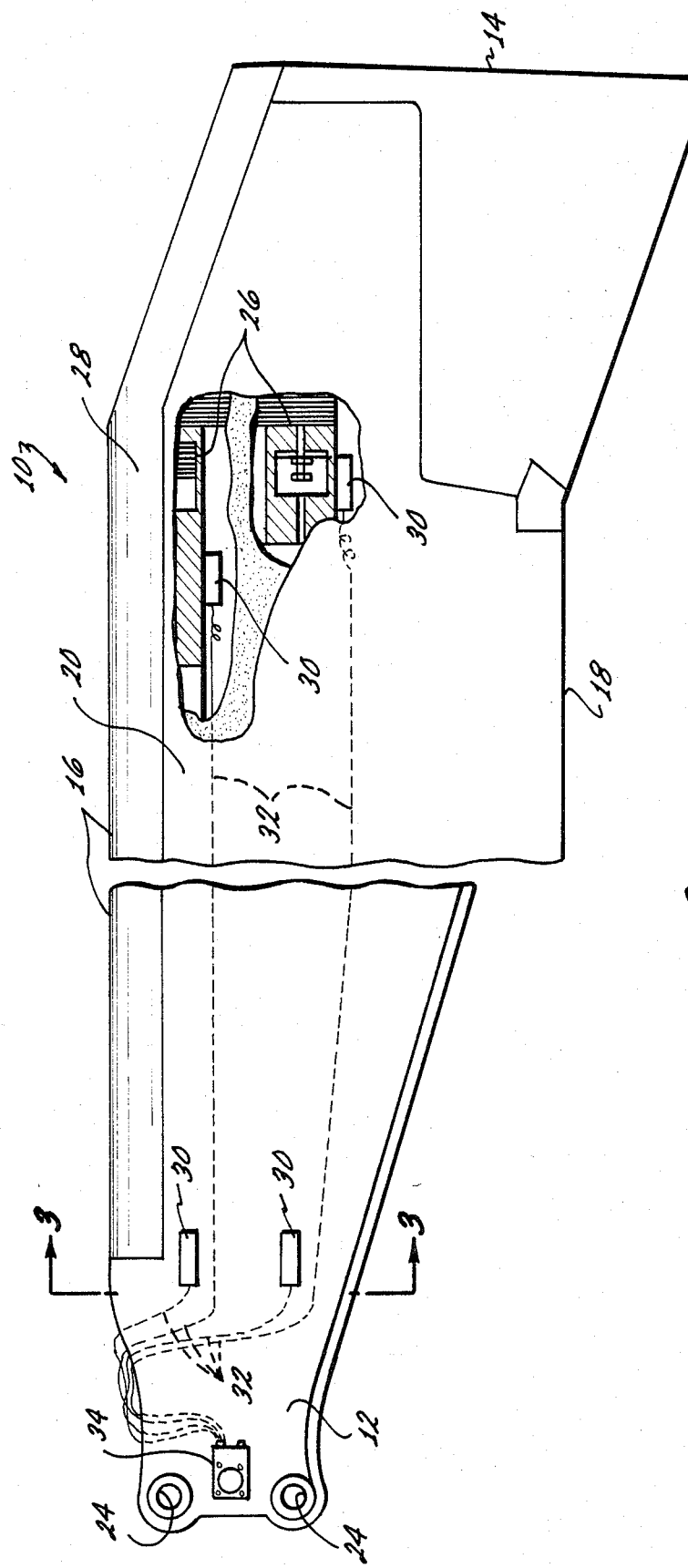
FIG. 2 illustrates typical positioning of acoustic emission transducer pairs near the root and the tip respectively of a main rotor blade.

With reference to the drawings and particularly FIG. 1 thereof a typical rotor blade 10 is mounted to the main rotor hub 11 of a helicopter (not shown in the drawings). The main rotor assembly comprises more than one such rotor blade 10 and in the rotor hub 11 suggested in FIG. 1 four such main rotor blades are required. The rotor blade 10 has a root end 12 which is secured to the rotor hub by means known to the art and which may vary according to the particular helicopter construction. The rotor blade also has a tip end 14 opposite the root end, a leading edge 16 and a trailing edge 18. A pair of curved skins extend between the leading and trailing edge and form the top and bottom aerodynamic surfaces 20, 22 respectively of the rotor blade. The construction of the rotor blade 10 may be appreciated in somewhat greater detail by reference to FIG. 2 in which the intermediate portion of the rotor blade has been broken away so as to illustrate an enlarged view the root end and a tip end thereof. The root end 12 of the rotor blade includes a pair of apertures 24 through which are inserted fasteners for securing the rotor blade to the rotor hub.

The rotor blade illustrated in the drawings is of the type which is presently manufactured of composite materials such as epoxy laminates of Kevlar fibers. Layers of such laminates are laid up over an internal framework of spar tubes which provide the desired shape to the upper and lower aero dynamic surfaces. The interior of the spar tubes and certain spaces there between the spar tubes are hollow. Some of the space is occupied by various weight assemblies for balancing the rotor blade. Two such adjustable weight assemblies 26 may be seen through the broken away portion of the upper aero dynamic surface 20. The rotor blade further comprises an erosion strip 28 affixed to the leading edge 16 of the rotor blade. This erosion strip is a sacrificial portion of the rotor blade in that it is subject to continuous erosion through collision with matter suspended in the air such as particles of water, ice, sand and dust. Given the high velocities at which such collisions take place, the erosion strip wears out after a certain length of use which varies with the environmental conditions and after which the erosion strip must be replaced. For this purpose the rotor blade 10 is removed from the rotor hub 12 and taken to a maintenance area. In the meantime, to avoid keeping the helicopter grounded during repairs to the rotor blade, a new or refurbished set of rotor blades is mounted to the rotor hub 12 and the helicopter is returned to service. After repairs are completed on the rotor blades they may then be mounted to the rotor hub of a second helicopter which will often be different from the first helicopter to which the blades were originally mounted. In effect the rotor blades are rotated among different helicopters through the useful life of the blades.

According to the present invention, an array of acoustic emission monitoring transducers 30 are mounted to the rotor blade and connected by means of conductors 32 to a connector unit 34 mounted at the root end of the blade. The connector unit is matable to a connector unit mounted to the rotor hub 12 such that the electrical outputs of the transducers 30 may be routed into the interior of the helicopter.

The connection of the conductors 32 to the cockpit instrumentation may be accomplished by means of collector slip rings mounted to the rotor hub 12 such as are known to the art and used to make electrical connections to deicer circuits provided in each of the rotor blades. In a rotor blade so equipped advantage can be taken of the existing deicer blanket circuitry to the extent of using commom ground wires shared by the deicing circuits and the acoustic emission transducer circuits. If desired, appropriate isolation circuits may be included so that the existing deicer conductors are completely shared between the deicer circuits and the acoustic emission sensors. The existence of the deicer circuits further faciliates the installation of the acoustic emission devices in that a slip ring will already have been provided on the rotor hub and can also be used for connecting the conductors 32 to corresponding conductors leading into the helicopter fuselage.

In the alternative, wireless transmitters of miniaturized construction may be mounted within the rotor blades for transmitting the acoustic emission information sensed by the transducers 30 by means of radio frequency signals to an appropriate radio receiver mounted in the helicopter fuselage.

The particular nature of the transducers 30 is not critical and may be selected from devices known to the art. Desirably, however, the transducers are of miniaturized construction so as not to upset the balance of the rotor blade and also minimize the centrifugal force experienced by the transducer.

The transducers 30 may be mounted interiorly to the rotor blade during assembly of the blade and co-cured with the composite material blade. In the alternative the transducers 30 may be secured to an external surface of the rotor blade, either the upper surface 20 or lower surface 22 and potted in a suitable adhesive or protective compound such as an epoxy. Such exterior mounting has the advantage of easy access to the transducers in the event that repair, replacement, or repositioning become desirable. The actual number of transducers 30 as well as the precise positioning of the transducers relative to the rotor blade are dependent on the construction of the particular rotor blade to be monitored as well as the quantity of information that is desired and that is capable of being processed by the system's electronics. For example, the system can be implemented at varing levels of sophistication spanning the range between a strategically positioned single transducer per blade to a multitransducer array coupled with an electronic processing system capable of localizing an impending failure through time analysis of the signals derived from the transducer array.

FIG. 1 illustrates in block diagram of a typical electronic processing and warning system for a helicopter. The conductors 32 are electrically connected by means of suitable terminals to a slip ring or equivalent device shown symbolically as connector 36 in FIG. 1. The transducer output signals taken from the connector 36 constitute an input to a receiver 38 whose function is to preprocess the signals from individual sensors so as to make the information intelligent for processing in an electronic filter 40. Among other things in one embodiment of this invention the receiver may multiplex the information received from the rotor assembly such that information from each individual blade is processed for 20 percent of the time in turn rather than continuously monitoring the acoustic emissions of all four blades in a typical four blade rotor. Such intermittent monitoring of the blades may be feasible where the type of critical noise indicative of irreversible progressive structural failure is a substantially continuous or relatively long duration acoustic emission. Where the critical acoustic emissions are short pulses then continuous monitoring of each blade in a rotor assembly may be necessary in order to accumulate an accurate stress history of each rotor blade.

The electronic filter 40 is constructed so as to discriminate against normal flight sounds for the particular aircraft in question. Thus, the particular helicopter will have non-critical acoustic emissions produced by normal rotation of the rotor, sounds generated by bearings, articulated joints, air friction and engine vibration etc. The filter allows the passage of critical waveforms having characteristic frequencies and amplitudes which, based on prior experimental data gathered during ground stress testing of sample rotor blades, are known to be indicative of over stress and structural damage to the composite material of the rotor blade.

When such known critical wave forms are detected and passed by the electronic filter 40 they constitute an input to a computer 42 which accumulates a count of such events. The computer in addition takes into account the "loudness" or intensity of each such critical wave form. Thus, these two criteria, namely, the count and the loudness of the critical wave forms constitute the data input to the computer from which an overall stress indication is derived for display to the aircraft crew and for activating various early warning devices in the event of dangerous overloads or failure of the rotor blades. Such over stresses would typically be associated with both a high count of critical wave forms and a high amplitude of the wave forms. While it is possible to subject the information derived from the acoustic emission transducers to extensive analysis capable of revealing the number of fractures and severity of each, in a practical system it will be desirable to maintain any in-flight analysis to a minimum consistent with providing an adequate level of confidence by the crew in the continued viability of the rotor system. If desired, a continuous in-flight recording of the acoustic emission transducer output may be kept and later subjected to more rigorous analysis on ground based equipment. Such analysis may include triangulation of acoustic emissions detected by the transducer array so as to calculate the location of any source of unusually loud or frequent critical acoustic emissions so as to enable quick repairs to be made without need for extensive searching and testing for the location of the fault.

In the preferred embodiment of the present invention, the computer 42 may be provided with a data input device such as a numerical key board 46. The purpose of such an input device is to enter a base count representative of the stress history of a refurbished rotor blade which is newly installed on a helicopter during the previously described rotation process. Absent such a data entry device the computer and stress indication and warning devices would provide false information unless the computer is provided with information regarding previous usage and stresses to which the refurbished rotor blade was subjected in service on other helicopters. The refurbishing mentioned above is limited to repairs which do not materially rejuvenate the load bearing portions of the rotor blade structure and are generally limited to cosmetic improvements such as repainting and resurfacing of the rotor blade or, for example, replacement of the erosion strip. More fundamental repairs to the rotor blade may require adjustment of the accumulated stress history for the rotor blade structure to reflect the renewed stress handling ability of the blade following such repairs. The data entry device 46 is shown as a numerical key board for entering values representative of accumulated critical acoustic emissions previously detected during use of the rotor blade on a first helicopter. The computer 42 of the system includes a data storage device such as a digital or analog memory in which is accumulated a count of critical acoustic emissions. This count is preferably continuously updated during flight and is weighted according to the amplitude of the critical signals so stored. The count may include separate figures for the frequency and amplitude of the critical acoustic emissions or may include a signle figure which combines the two criteria. The accumulated count stored in the afore said data storage in the computer 42 is displayed to the helicopter crew preferably by means such as stress indicator 48 which displays the accumulated count as a percentage of a predetermined maximum safe figure. In addition the count accumulated by computer 42 may be connected to a visual or audible cockpit signal or warning device 50 for calling immediate attention to any unusual pattern of acoustic emission signals such as may be indicative of severe overstress or of impending catastrophic structural failure of the rotor blade.

The stress indicator 48 may be connected so as to sequentially display the stress status of each individual rotor blade in the helicopter's rotor assembly or in the alternative a number of such stress indicators may be provided, each dedicated to a particular rotor blade. The entry device 46 may take forms other than the keyboard shown in FIG. 1, such as variable resistances which may be set to provide an analog input corresponding to a previously accumulated stress count for a particular rotor blade.

The present invention thus makes it feasible to provide real time in-flight monitoring of interchangable dynamic components such as helicopter rotor blades while allowing for periodic removable of the rotor blades from the aircraft and returning the components to service on aircraft which may be different than the one on which the blades were first used. It is understood that the blades may be replaced on the same aircraft from which they were earlier removed but the aircraft may have been flown, in the meantime using an alternative set of rotor blades. In that event, the accumulated stress history retained in the data storage device of computer 42 representative of the stress history of the rotor blades during its initial period of service will have been erased by appropriate means and new data pertaining to the replacement set of blades entered in its place. Prior to erasure the accumulated stress history of the removed set of blades is entered into an alternate data storage device such as a ground based information system which may include digitial computers or manual entry log books. Upon returning the refurbished set of blades to service the recorded stress history is retrieved from the alternate information system and entered by means of the data entry device 46 into the data storage of computer 42 of the helicopter in which the blades are to be installed so as to provide base data of the stress history of the rotor blades.

In an alternate embodiment of the invention the computer, indicator and alarm devices may be omitted from the system and the transducer output merely recorded on a recording device 44 such as a magnetic tape recorder for subsequent analysis on the ground. While such a system would not provide real time monitoring of the soundness of the rotor blades it will nevertheless represent a marked improvement over the present approach to blade replacement after an arbitrary number of flight hours. In such an embodiment of the invention, the tape or other recording medium is removed from the recorder 44 at periodic intervals, preferably following each flight, played back and subjected to analysis. The results of the analysis which may include the afore mentioned criteria of frequency and amplitude of critical wave forms is stored in a data storage device such as a computer memory or entered manually in a log book or equivalent record. Thus, replacement of the rotor blades may be carried out based on a more realistic accumulated stress history for each individual rotor blade rather than some arbitrary number of flight hours having no relationship to actual conditions of usage of the particular rotor blade.

It must be understood that many alterations modifications and substitutions may be made by those having ordinary skill in the art to both the apparatus and method of the present invention without departing from the spirit and scope of the invention. Therefore, the presently illustrated embodiment has been shown only by way of example and for purposes of clarity and should not be taken to limit the scope of the following claims.

We claim:

1. Apparatus for determining the actual useful life of interchangeable helicopter blades comprising:
    means associated with a particular helicopter rotor blade for monitoring acoustic emissions emitted by said rotor blade under operating stress;
    computer means associated with said helicopter for accumulating a count of monitored acoustic emissions indicative of progressive structural failure of said interchangeable helicopter rotor blade, said computer means including data storage means for storing said count of acoustic emissions, and input means for entering a base count indicative of acoustic emissions emitted by said rotor blade during use prior to installation in said particular helicopter; and
    indicator means for warning the crew of said helicopter of a cumulative count and/or stress level approaching a predetermined acoustic emission count associated with catastrophic failure of similar rotor blades such that the actual useful life of said rotor blade may be exhausted prior to actual rotor blade failure.

2. The apparatus of claim 1 wherein said mounting means comprise transducer means mounted to said rotor blade, and
    detachable electrical connector means for interconnecting said transducer means to said computer.

3. Apparatus for determining the actual useful life of interchangeable helicopter blades comprising:
    one or more transducers mounted to a particular interchangeable rotor blade for generating an electrical output responsive to acoustic emissions of said rotor blade;
    computer means associated with a particular helicopter for accumulating a count of acoustic emissions indicative of progressive structural failure of said rotor blade;
    input means for entering a base count indicative of acoustic emissions emitted by said rotor blade during use prior to installation in said particular helicopter;
    detachable electrical connector means interconnecting said transducer means to said computer means; and
    indicator means associated with said particular helicopter for indicating to the crew of said helicopter a continuously updated cumulative count of acoustical emissions in relation to a predetermined acoustic emissions count associated with imminent catastrophic structural failure of said rotor blade.

4. Method for measuring the actual remaining useful life of interchangeable helicopter rotor blades comprising:
    installing a particular rotor blade on a first helicopter;
    detecting acoustic emissions emitted by said rotor blade under operating stress indicative of progressive structural failure of said rotor blade;
    accumulating a count of said acoustic emissions;
    storing said count in a memory associated with said first helicopter;
    removing said rotor blade;
    installing said rotor blade on a second helicopter;
    entering said stored count in a memory associated with said second helicopter;
    detecting further acoustic emissions emitted by said rotor blade under operating stress indicative of continued progressive structural failure of said rotor blade;
    adding said detected further emissions to said stored count; and
    displaying said stored count for viewing by crew members of said second helicopter whereby the crew of said second helicopter may be forwarned prior to accumulating an acoustic emission count associated with imminent catastrophic structural failure of said rotor blade.

* * * * *